US00PP37712P2

(12) United States Plant Patent
Hansen

(10) Patent No.: US PP37,712 P2
(45) Date of Patent: Sep. 22, 2026

(54) *SALVIA* PLANT NAMED 'Dark Sky'

(50) Latin Name: ***Salvia* hybrid**
Varietal Denomination: Dark Sky

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,047

(22) Filed: Feb. 25, 2026

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
CPC ... A01H 5/02; A01H 5/00; A01H 5/12; A01H 6/508; A01H 6/50
See application file for complete search history.

(56) References Cited

U.S. PATENT DOCUMENTS

PP20,456 P2 * 11/2009 Oudolf ..... Plt./475
PP29,498 P2 * 7/2018 Hansen ..... Plt./475

* cited by examiner

*Primary Examiner* — June Hwu

(57) ABSTRACT

A new and distinct cultivar of perennial *Salvia* plant named 'Dark Sky' characterized by its large, mounded, vigorous, and winter-hardy habit. The large flowers of deep indigo-blue beginning in late spring on densely arranged in verticils on tall, stiff, heavily-branched panicles above a mound of large, rugose, dark-green foliage. The new plant flowers without vernalization. *Salvia* 'Dark Sky' is useful for ornamental purposes.

2 Drawing Sheets

Botanical denomination: *Salvia* hybrid.
Cultivar designation: 'Dark Sky'.

STATEMENT REGARDING PRIOR DISCLOSURES UNDER 37 CFR 1.77(B)(6)

The first offer for sale of *Salvia* 'Dark Sky' was Walters Gardens, Inc. to Centerton Nursery, Inc. on Apr. 8, 2025. The new plant was later disclosed in the form of a photograph and brief description on a website operated by Walters Gardens, Inc. on Dec. 1, 2025. Walters Gardens, Inc. obtained the plant and all information relating thereto from the inventor. No plants of *Salvia* 'Dark Sky' have been sold in this country or anywhere in the world, nor has any disclosure of the new plant been made, more than one year prior to the filing date of this application, and such sale or disclosure would be a 35 U.S.C. § 102(b) exception.

BACKGROUND OF THE INVENTION

The present invention relates to a new and distinct cultivar of ornamental sage plant hereinafter referred to by the cultivar name *Salvia* 'Dark Sky' or as the new plant. The new plant was a single seedling selection from a cross between the proprietary hybrid known only as 19-9-1 (not patented) as the female or seed parent and the proprietary hybrid known only as 15-9-2 (not patented) as the male parent is at a wholesale perennial nursery in Zeeland, Michigan, USA. The cross was performed on Jul. 4, 2020, the seed was collected on Aug. 24, 2020, and sown at the same nursery. The new plant was initially evaluated in the summer of 2021 and assigned the breeder code 20-3-9 through the trial process prior to assigning the cultivar name.

The new *Salvia* was further evaluated and asexually propagated initially by division in 2021 and later by basal cuttings taken at the same nursery in Zeeland, Michigan. Evaluation of these and further cutting grown plants shows that *Salvia* 'Dark Sky' continues to be stable and produce true to type plants in successive generations of asexual propagation.

SUMMARY OF THE INVENTION

Plants of *Salvia* 'Dark Sky' have not been observed under all possible environmental conditions. The phenotype may vary somewhat with variations in environment such as temperature, nutrition and light intensity without, however, any variance in genotype.

The closest comparison plants known to the inventor are: 'Big Sky' U.S. Plant Pat. No. 37,290, 'Evening Attire' U.S. Plant Pat. No. 32,573, 'Madeline' U.S. Plant Pat. No. 20,456, and 'Midnight Model' U.S. Plant Pat. No. 29,498.

'Big Sky' has a slightly taller and broader habit and the flowers are similar size but lighter violet-blue colored. 'Evening Attire' has a smaller habit, smaller foliage, flower buds of dark violet-blue, and flowers that are dark violet-blue. 'Madeline' has a larger more open habit, and the smaller flowers are two-toned with white and dark bluish-purple. 'Midnight Model' has smaller flowers that are violet-blue with smaller foliage on smaller plants. Each of the listed comparison plants flowers earlier in the season than the new plant.

The female parent is much taller with flowers that are a lighter bluish-purple. The male parent is also much taller, has dark blue flowers and the flowering season is later. Both parents had flower verticils that are spaced further apart.

The following characteristics in combination distinguish *Saliva* 'Dark Sky' as a new and distinct cultivar from all other cultivars known to the inventor:

1. Large, mounded, vigorous, and winter-hardy habit, herbaceous perennial;
2. Large flowers of deep indigo-blue densely arranged in verticils;
3. Flowering on stiff, upright, heavily-branched panicles beginning in late spring without vernalization;
4. Stems and sepals have purplish anthocyanin pigmentation in high ultraviolet light;
5. Large, rugose, clean, dark-green foliage.

BRIEF DESCRIPTION OF THE DRAWINGS

The photographs of the new plant demonstrate the unique traits and the overall appearance of *Salvia* 'Dark Sky'. The colors are as accurate as reasonably possible with color reproductions. Variation in ambient light spectrum, source and direction may cause the appearance of minor variation in color. The plant used in the photographs was a three-year-old plant grown at a wholesale perennial nursery in Zeeland, Michigan with supplemental water and fertilizer when needed.

DETAILED BOTANICAL DESCRIPTION

Figure 1:
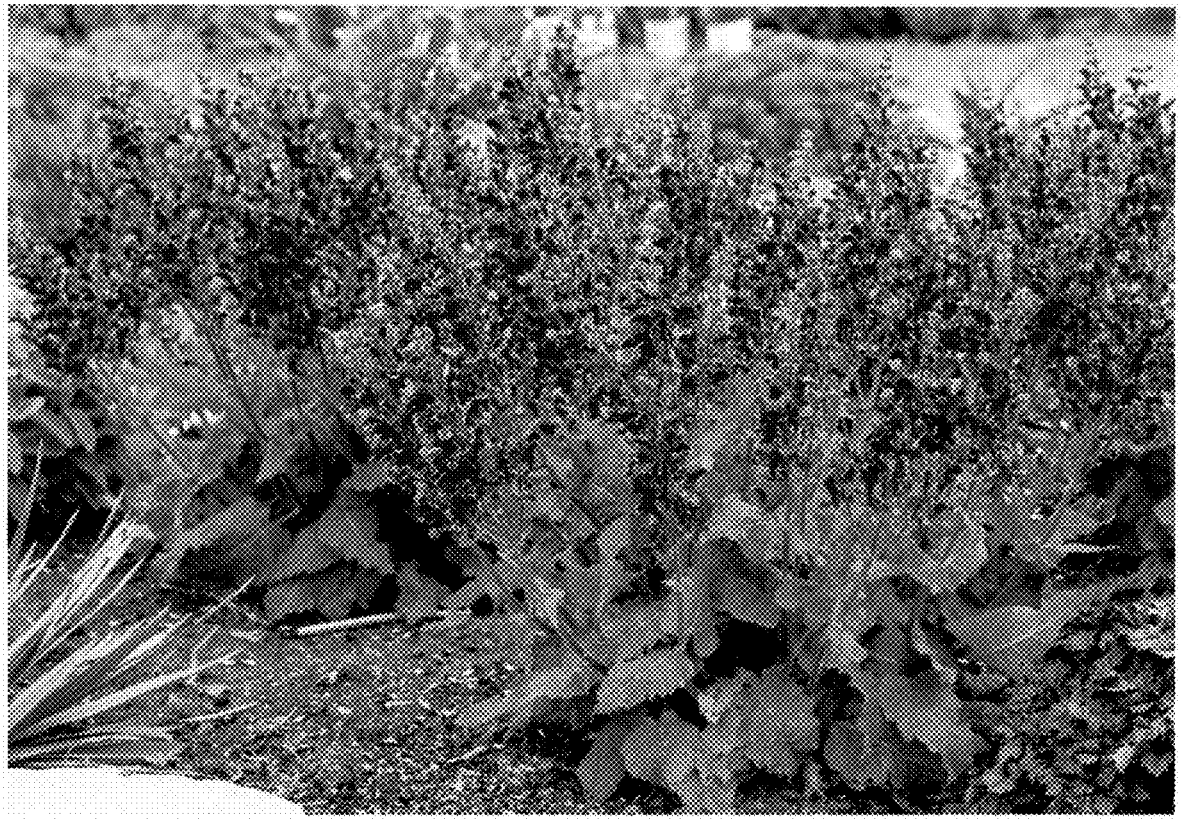
FIG. 1 shows the plant habit in full flower in a an open, full-sun trial garden landscape.
Figure 2:
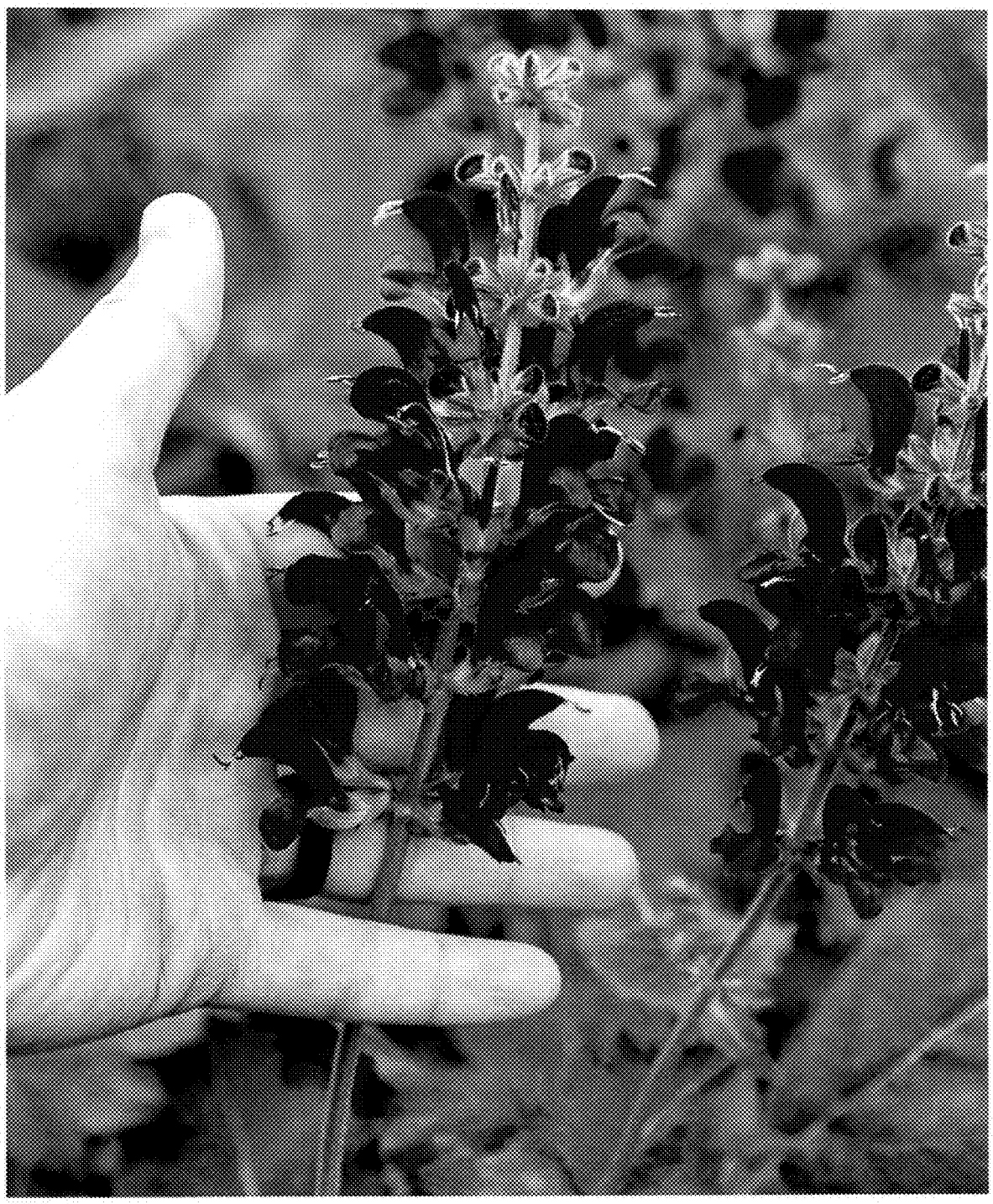
FIG. 2 shows a close-up of the flower scape with the buds, flowers, stems and calyxes in a partially shaded greenhouse.

The following descriptions and color references except where common dictionary terms are used are based on the 2015 edition of The Royal Horticultural Society Colour Chart. *Salvia* 'Dark Sky' has not been observed under all possible environments. The phenotype may vary slightly with different growing environments such as temperature, light, fertility, soil pH, moisture and plant maturity levels, but without any change in the genotype. The following observations and size descriptions are based on three-year old plants growing in an outdoor full-sun trial garden at a wholesale perennial nursery in Zeeland, MI. Plants were given supplemental water and fertilizer as needed.

Botanical classification: *Salvia* hybrid;

Parentage: Female or seed parent is 19-9-1; male or pollen parent is 15-9-2;

Plant habit: Winter-hardy herbaceous perennial; multi-stemmed, compact, rounded, with mostly basal foliage, and flowers in several tightly arranged verticils on branched upright racemes displayed above foliage; in flower with panicles about 62 cm tall and about 73 cm wide at the fullest point about 40 cm above soil; cauline foliage extends up the stems about 38 cm; about 24 flowering panicles per plant;

Propagation: By basal vegetative shoot cuttings; time to produce a rooted stems about two weeks;

Growth rate: Rapid, vigorous, finishing in a 3.8-liter container in about 12 weeks from a 25 mm plug;

Root description: Fine, well-branched; color dependent on age and soil type, from cream to dark tan in color depending on age and soil matrix;

Foliage: Opposite; simple; moderately rugose; lanceolate; margin irregularly crenate; adaxial surface glabrous, and abaxial micro-puberulent; acute apex and base cordate, with lobes not overlapping; leaf blades to about 24 cm long and 13 cm across, cauline leaves decreasing in size distally; average about 20 cm long and 8.5 cm across;

Foliage color: Young adaxial between RHS 146B and RHS 147B, young abaxial surface between RHS N138C and RHS 194B; mature adaxial between NN137A and RHS NN137B, mature abaxial between RHS N138C and RHS 194B;

Venation: Reticulate; slightly impressed on adaxial side and costate on abaxial side; midrib adaxial and abaxial pubescent; adaxial secondary veins glabrous; abaxial secondary veins puberulent;

Vein color: Adaxial midrib between RHS 148D and RHS 147D, adaxial primary and secondary veins nearest RHS 148C; abaxial midrib and primary veins between RHS 138B and RHS 193A, abaxial secondary veins between RHS N138C and RHS 194B;

Petiole: Slightly concavo-convex; puberulent; to about 11 cm long and 11 mm wide, average 7 cm long and 6 mm wide at base;

Petiole color: Adaxial between RHS 148D and RHS 145D; abaxial between RHS 145D and RHS 147D; developing a moderate to strong blush on adaxial of nearest RHS 183B with intense light;

Flower description: Perfect; bilabiate; zygomorphic; fused corolla portion glabrous adaxial and puberulent abaxial;

Flower size: 33 mm long to tip of exserted stigma, 21 mm tall, 13 mm wide; corolla 20 mm long, 21 mm tall, 13 mm wide; corolla tube fused in the basal 17 mm long, 7 mm tall and 3 mm wide;

Inflorescence: Panicle; with up to 6 primary and 2 secondary branches; branched at about 45° angle; flowering portion to 36 cm long and 28 cm wide; branches to 26 cm long and 3 mm across base; verticillate with flowering generally beginning at lower verticils and advancing up the scape, but not all flowers at each verticil opening at the same time giving the effect of a scape being in continuous flower for longer periods; typically five to six flowers per verticil; average distance between verticils about 12 mm, greater proximally and less distally; about 16 verticils per main stem; about 200 to 300 flowers per panicle;

Flowering period: Flowering beginning late spring for about six weeks and repeating if initial inflorescences removed;

Peduncle: Quadrangular with longitudinal furrows on each side; heavily pubescent to glandular; to 46 cm long and 8 mm across at base;

Peduncle color: Proximal portion between RHS 146B and RHS 138B moderately maculate with nearest RHS 187A, distal portion heavily maculate to near solid nearest RHS 187A;

Flower aspect: Flower midline projected about 30-degree angle above horizontal and hood petal about 60-degree angle above horizontal;

Flower longevity: About four days on the plant or as cut flower; calyx persistent; self-cleaning, corolla, pistil, and stamen not persistent;

Flower fragrance: None detected under present growing conditions;

Flower buds one day prior to anthesis: Arcuate downward; with rounded apex; pubescent; corolla about 27 mm long, 15 mm tall and 3 mm wide;

Bud color: Exposed dorsal petals darker than RHS N92C or RHS N92B; ventral petals distally between RHS N89B and RHS N89C, exposed proximal portion between RHS 84C and RHS 84D, and lateral portion nearest RHS N87A; abaxial calyx nearest RHS 138B ventrally with some veins nearest RHS N187A, dorsally nearest RHS N187A;

Petals: Bilabiate corolla consisting of an upper cucullate and lower labium with three lobes; Upper petal: glandular abaxial, glabrous adaxial; about 27 mm long including fused base, 7 mm tall, and 2 mm across, extending 17 mm beyond fusion point; folded along longitudinal axis; apex rounded and emarginate, with 1 mm deep notched apex and base fused with labium in proximal 10 mm;

Hood color: Adaxial distally between RHS N89A and RHS N89B, progressing to between RHS 85B and RHS 85C in the proximal center before corolla tube; abaxial darker and more violet than RHS N92B and RHS N92C;

Labium (lower) petal: Consisting of three lobes, two proximal side lobes and larger center lobe;

*Center lobe*.—Obcordate, cupped; rounded emarginate apex with notch about 3 mm deep; margin crenulate; base micro-puberulent in the distal abaxial center, glabrous adaxial and outer abaxial margin; size about 26 mm long including fused base extending 16 mm beyond fusion point; natural width 12 mm and when spread to 15 mm.

*Center lobe color*.—Adaxial and abaxial between RHS 93A and RHS 93B.

*Side lobes*.—Lanceolate; apices acute; base fused to corolla tube; revolute; puberulent to glandular in the abaxial longitudinal center, glabrous adaxial and along the abaxial margins; size about 5 mm long from fusion and 3 mm wide.

*Side lobes color*.—Adaxial and abaxial between RHS 93A and RHS 93B.

*Corolla tube color*.—Lighter than RHS 85D.

Androecium: Two, adnate with corolla in proximal 11 mm; contained within hood petal except distal 7 to 9 mm;

*Filament*.—Two; glabrous; lustrous; cylindrical; fused in basal 11 mm of corolla tube; arcuate about 11 mm long around inside of hood petal; about 29 mm long and about 0.7 mm diameter near base with a 2 mm long trip mechanism at base; color nearest RHS 85A; color of trip mechanism between RHS 85A and RHS 85B.

*Anther*.—Glabrous; oblong ellipsoidal; dorsifixed; longitudinal; about 4 mm long and 1 mm diameter; color between RHS N186C and RHS N187B.

*Pollen*.—Abundant; less than 0.1 mm; color nearest RHS 9B.

Gynoecium: One, arcuate around inside of hood petal;

*Style*.—Cylindrical; glabrous; lustrous; exserted; to about 40 mm long and 0.5 mm diameter; color nearest RHS NN155D in proximal three-quarters, transitioning in the distal one-quarter to nearest RHS 86B just before stigma.

*Stigma*.—Bifurcate; cylindrical with an acute apex; to about 3 mm long and about 0.3 mm diameter; color between RHS N89A and RHS 86A.

*Ovary*.—Superior; four ovules; color nearest RHS 145C.

*Fruit*.—Rounded to ellipsoidal and slightly flattened; glabrous; matte surface; to about 2 mm long, 1.5 mm across, and 1 mm thick; color at maturity nearest RHS 200A.

Calyx: Campanulate; about 11 mm long and 7 mm tall at mouth and 5.5 mm wide; fused in basal 7 mm; lower set bifurcate in distal 3 mm; upper set trifurcate in distal 0.5 mm;

Sepals: Five, three upper and two lower; lanceolate; acute apex; basal 7 mm fused;

Sepal color: Adaxial distally nearest RHS 137A with veins nearest RHS NN 137, proximally between RHS 145D and RHS 145C with veins nearest RHS NN137C; abaxial nearest RHS 138B ventrally with some veins nearest RHS N187A, dorsally veins between RHS N77A and RHS N187A;

Bracts: Each verticil and branch subtended by two opposite deltoid bracts; apex narrowly acute to acuminate; base sessile and truncate; margin crenate and ciliolate; glabrous adaxial and pubescent abaxial; verticil bract size up to 11 mm long and 8 mm wide, branch bract to 52 mm long and 55 mm wide; both verticil and branch bracts decreasing distally;

Bract color: Adaxial nearest NN137B, abaxial nearest RHS 137A;

Pedicels: Cylindrical; puberulent to glandular; short, to about 1 mm long and 1 mm diameter; aspect outwardly to slightly upward;

Pedicel color: Variable; nearest RHS N79B in high light exposure, nearest RHS N148C in lower light exposure;

Culture: Plants of *Salvia* 'Dark Sky' perform best with adequate moisture and good drainage and are hardy from USDA zone 3 to 8.

Disease and pest resistance: Resistant and susceptibility to diseases and pests beyond that common to *Salvia* has not been noted.

It is claimed:

1. A new and distinct perennial *Salvia* plant named 'Dark Sky' as herein described and illustrated.

* * * * *